United States Patent
Wang

(10) Patent No.: US 8,217,181 B2
(45) Date of Patent: Jul. 10, 2012

(54) DIHALOGEN INDOLOCARBAZOLE MONOMERS AND POLY (INDOLOCARBAZOLES)

(75) Inventor: Hailiang Wang, Camarillo, CA (US)

(73) Assignee: E. I. Du Pont De Nemours and Company, Wilmington, DE (US)

( * ) Notice: Subject to any disclaimer, the term of this patent is extended or adjusted under 35 U.S.C. 154(b) by 0 days.

(21) Appl. No.: 12/793,899

(22) Filed: Jun. 4, 2010

(65) Prior Publication Data

US 2011/0060097 A1 Mar. 10, 2011

Related U.S. Application Data

(62) Division of application No. 11/303,582, filed on Dec. 16, 2005, now abandoned.

(60) Provisional application No. 60/640,482, filed on Dec. 30, 2004, provisional application No. 60/694,916, filed on Jun. 28, 2005.

(51) Int. Cl.
*C07D 487/22* (2006.01)
(52) U.S. Cl. ....................................................... 548/418
(58) Field of Classification Search .................... 548/418
See application file for complete search history.

(56) References Cited

U.S. PATENT DOCUMENTS

| | | | |
|---|---|---|---|
| 5,843,607 A | 12/1998 | Hu et al. | |
| 5,942,340 A | 8/1999 | Hu et al. | |
| 5,952,115 A | 9/1999 | Hu et al. | |
| 6,303,238 B1 | 10/2001 | Thompson et al. | |
| 7,173,140 B2 | 2/2007 | Li et al. | |
| 2001/0019782 A1 | 9/2001 | Igarashi et al. | |

FOREIGN PATENT DOCUMENTS

| | | | |
|---|---|---|---|
| DE | 19831427 | * | 1/2000 |
| EP | 1191612 A2 | | 3/2002 |
| EP | 1191614 A2 | | 3/2002 |
| WO | WO 00/70655 | | 11/2000 |
| WO | WO 01/41512 A1 | | 6/2001 |
| WO | WO 02/02714 A2 | | 1/2002 |
| WO | WO 02/15645 A1 | | 2/2002 |

OTHER PUBLICATIONS

Derwent translation of Richter et al. (DE 19831427, pub-date: Jan. 13, 2000).*
Hu et al. (SYNLETT, (2005), No. 1, pp. 42-48 [Advanced online publication: Nov. 29, 2004]).*
Wakim et al. (Chem. Mater. 2004, 16, 4386-88).*
Bradley et al., "Origin of electrophosphorescence from a doped polymer light emitting diode" in Synth. Met. May 2001, 116(1-3), 379-383.
Campbell et al., "Excitation Transfer Processes in a Phosphor-Doped Poly(p-phenylene vinylene) Light-Emitting Diode", Physical Review B., Feb. 2002, 65.
Gustaffson et al., "Flexible Light-Emitting Diodes made from Soluble Conducting Polymer", Nature, Jun. 11, 1992 357, 477-479.
Markus, Electronics and Nucleonics Dictionary, McGraw-Hill, 1966, 470 and 476.
O'Brien, et al., "Electrophosphoresence from a Doped Polymer Light Emitting Diode", Synthetic Metals, 2001, 116(1-3), 379-383.
Wang, Kirk Othmer Encyclopedia of Chemical Technology, 4th Edition, 1996, 18, 837-860.

* cited by examiner

*Primary Examiner* — Robert Havlin
(74) *Attorney, Agent, or Firm* — Woodcock Washburn LLP

(57) ABSTRACT

Monomers and polymers based on dihalogen indolocarbazole and poly(indolocarbazoles), and methods of making such and using the same are described, as well as organic electronic devices incorporating the same.

5 Claims, 17 Drawing Sheets

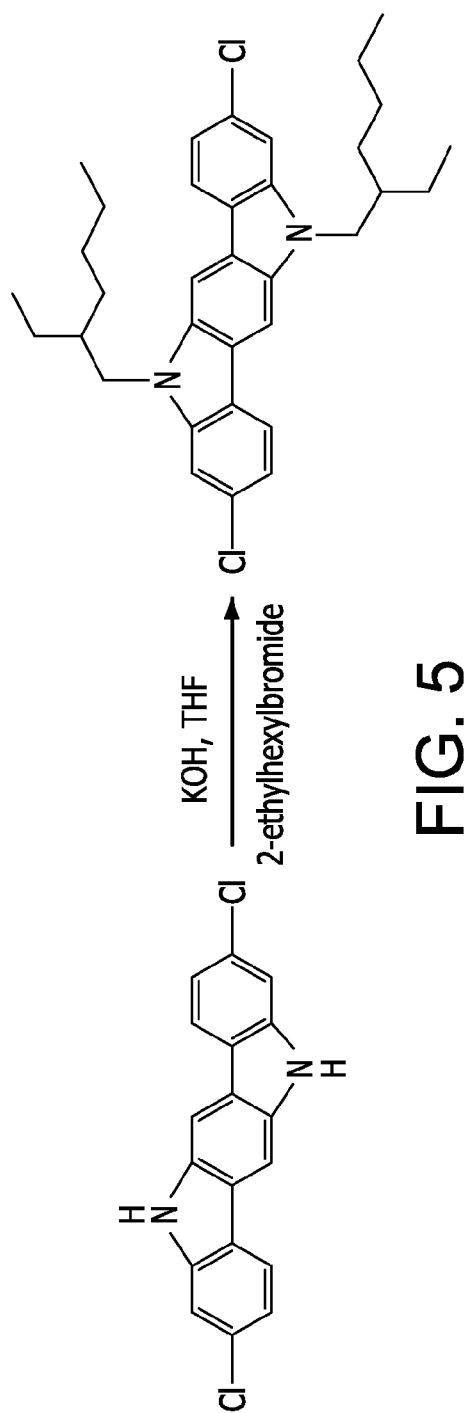
FIG. 5
FIG. 6

DIHALOGEN INDOLOCARBAZOLE MONOMERS AND POLY (INDOLOCARBAZOLES)

CROSS REFERENCE

This application is a divisional of U.S. patent application Ser. No. 11/303,582, filed Dec. 16, 2005, the disclosure of which is incorporated herein by reference in its entirety, and this application also claims benefit to U.S. Provisional Application Ser. Nos. 60/640,482, filed Dec. 30, 2004, and 60/694,916, filed Jun. 28, 2005, the disclosures of which are both incorporated herein by reference in their entireties.

FIELD

This disclosure relates generally to dihalogen indolocarbazole monomers and polymers and poly(indolocarbazoles), for example, those found in organic electronic devices, and materials and methods for fabrication of the same.

BACKGROUND

Organic electronic devices convert electrical energy into radiation, detect signals through electronic processes, convert radiation into electrical energy, or include one or more organic semiconductor layers. Charge transport materials facilitate migration of positive or negative charges through the organic device with relative efficiency and small loss of charges.

Thus, charge transport materials are important for the fabrication of organic electronic devices, and their development is a goal in the industry.

SUMMARY

Provided are dihalogen indolocarbazole monomers having a Formula I or II:

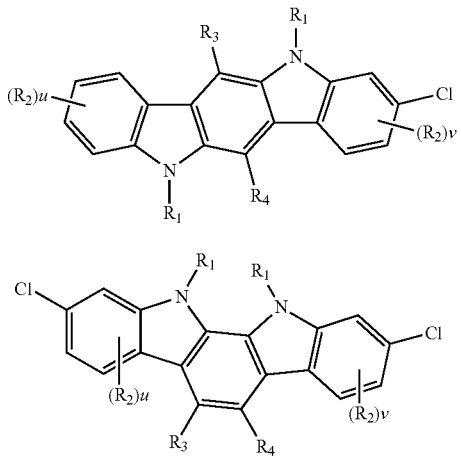

wherein $R_1$-$R_4$ are, independently at each occurrence, alkyl, heteroalkyl aromatic, or heteroaromatic groups, and u and v are independently 1, 2, or 3. The monomer is selected from a cis isomer (Formula II) or a trans isomer (Formula I). Polymers made therefrom, organic electronic devices or articles of manufacture incorporating, and methods of making the same are also provided.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

FIG. 5 shows the reaction scheme for synthesis of N,N'-Di (2'-ethylhexyl)-3,9-dichloro-5,11-dihydroindolo[3,2-b]carbazole.

FIG. 6 shows the reaction scheme for synthesis of N,N'-Di (2'-ethylhexyl)-3,8-dichloro-5,6-dihydromdolo[1,2-b]carbazole.

The figures are provided by way of example and are not intended to limit the invention. Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Monomers and polymers based on dihalogen indolocarbazole and poly(indolocarbazoles) are disclosed. In one embodiment, the polymers offer high molecular weight and/or good solubility and/or a fully conjugated main chain. In another embodiment, the polymers offer charge transport characteristics, for example, hole transport; and are neutral. In an embodiment, the polymers can be used in organic electronic devices, such as organic light-emitting diodes (OLEDs), for use in charge transport layers.

Provided are dihalogen indolocarbazole monomers having a structure according to Formula I or II

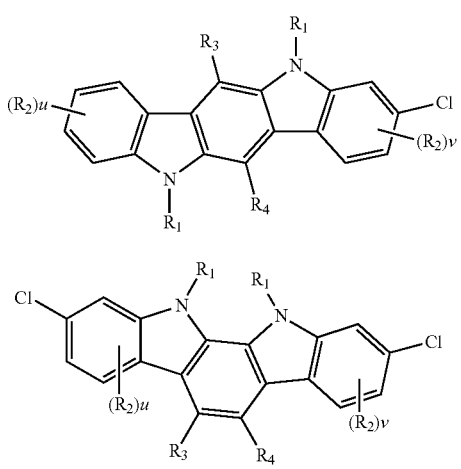

wherein $R_1$-$R_4$ are, independently at each occurrence, alkyl, heteroalkyl aromatic, or heteroaromatic groups, and u and v are, independently, 1, 2, or 3.

In one embodiment, one or more nonadjacent methyl or methylene groups can be replaced by —O—, —S—, —NR'—, or an aromatic or heteroaromatic ring.

In some embodiments, the monomers include 1,4-Bis(2'-nitro-4'-chlorophenyl)benzene; 3,9-Dichloro-5,11-dihydromdolo[3,2-b]carbazole; N,N'-Di(2'-ethylhexyl)-3,9-dichloro-5,11-dihydroindolo[3,2-b]carbazole; N,N'-Di(2'-ethylhexyl)-3,8-dichloro-5,6-dihydromdolo[1,2-b] carbazole; N,N'-bis[2-[2-(2-methoxyethoxy)ethoxy]ethyl]-3,9-dichloro-5,11-dihydroindolo[3,2-b]carbazole; or derivatives thereof.

Figure 1:
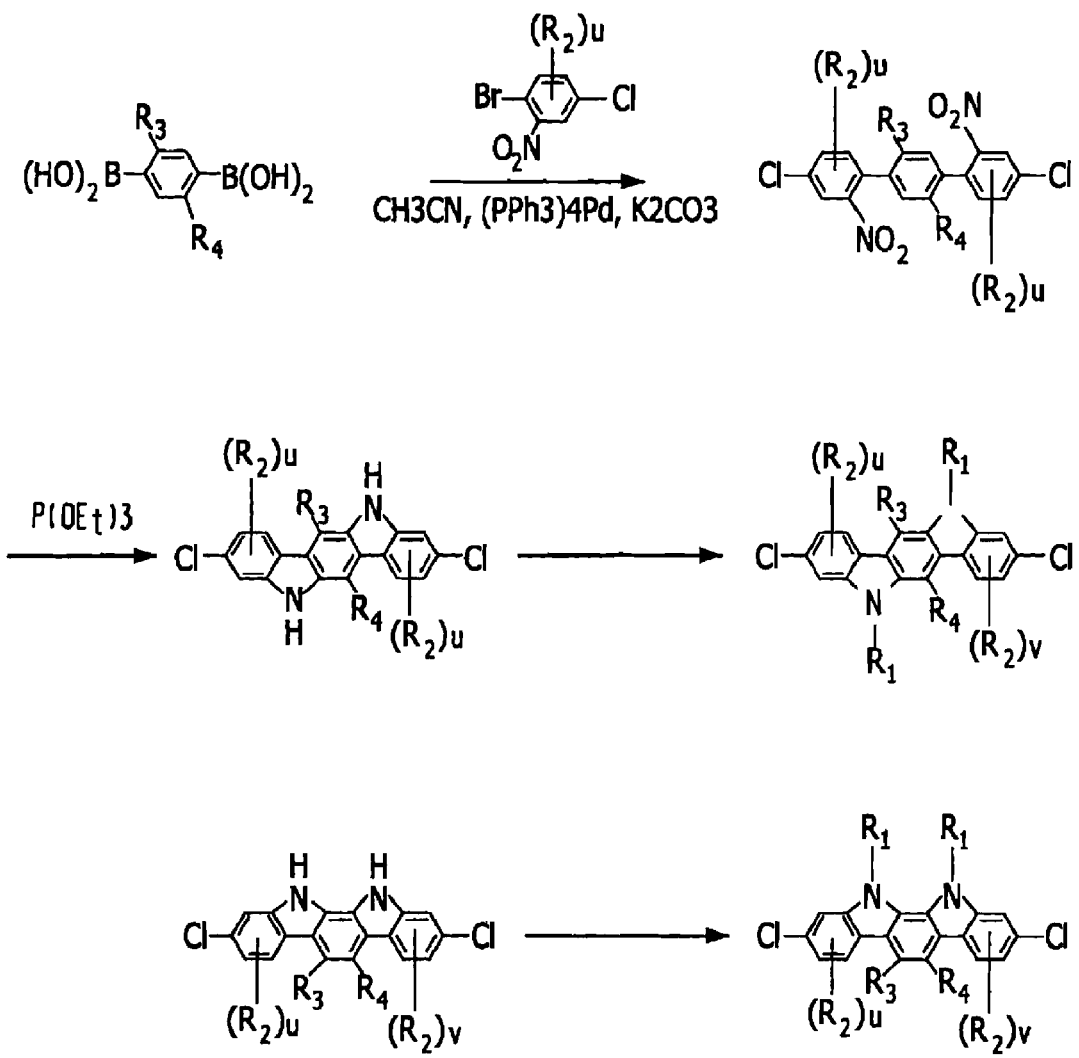
FIG. 1 shows a synthesis route for a dihalogen indolocarbazole, specifically, dichloroindolocarbazole, by a three-step reaction.

A method of making dihaloindolocarbazole monomers, in one embodiment, comprises reacting a first aromatic compound comprising $R_3$ and $R_4$ and a second aromatic compound comprising $R_2$ and a halogen with a first catalyst to form a first intermediate aromatic compound comprising $R_2$, $R_3$ and $R_4$; mixing a second catalyst with the first intermediate compound to form a second intermediate aromatic compound comprising $R_2$, $R_3$ and $R_4$; and mixing the second intermediate aromatic compound with $R_1$ to form a dihalogen indolocarbazole monomer; wherein: $R_1$-$R_4$ are, independently at each occurrence, alkyl, heteroalkyl aromatic, or heteroaromatic groups, and u and v are, independently, 1, 2, or 3. One detailed embodiment of making a dichloroindolocarbazole, by a three-step reaction, is depicted in FIG. 1.

In the methods of making the monomers of the disclosure, the first catalyst mixture comprises, for example, $CH_3CN$, $PPh_3$, $(PPh_3)_4Pd$, $K_2CO_3$, KOH, THF, 2-ethylhexylbromide, 2-[2-(2-methoxyethoxy)ethoxy]ethylbromide, toluene, or combinations thereof. In one example, the second catalyst mixture comprises $P(OEt)_3$.

In one embodiment, the above-described monomers are used to make oligomers.

In one embodiment, the above-described monomers are used to form a polymer. In some embodiments, the polymers include Poly(N,N'-Di(2'-ethylhexyl)-5,11-dihydroindolo[3,2-b]carbazole); Poly{N,N'-bis[2-[2-(2-methoxyethoxy)ethoxy]ethyl]-5,11-dihydroindolo[3,2-b]carbazole}; Poly{N,N'-bis[2-[2-(2-methoxyethoxy)ethoxy]ethyl]-5,11-dihydroindolo[3,2-b]carbazole-co-[2-[2-(2-methoxyethoxy)ethoxy]ethoxy]-phenylene}; Poly{N,N'-bis[2-[2-(2-methoxyethoxy)ethoxy]ethyl]-5,11-dihydroindolo[3,2-b] carbazole-co-9,9-bis[2-[2-(2-methoxyethoxy)ethoxy]ethyl]-fluorene}; Poly{9,9-bis[2-[2-(2-methoxyethoxy)ethoxy] ethyl]fluorene}; poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole}, wherein n is greater than 20; combinations thereof, conjugates thereof, or derivatives thereof.

In one embodiment, the polymers are used to make copolymers. In another example, the polymers comprise block copolymers. In still another embodiment, the monomers are used to make homopolymers.

In some embodiments, the polymers are used to form a layer in an organic electronic device.

The general structures of charge transport polymers based on indolocarbazole are:

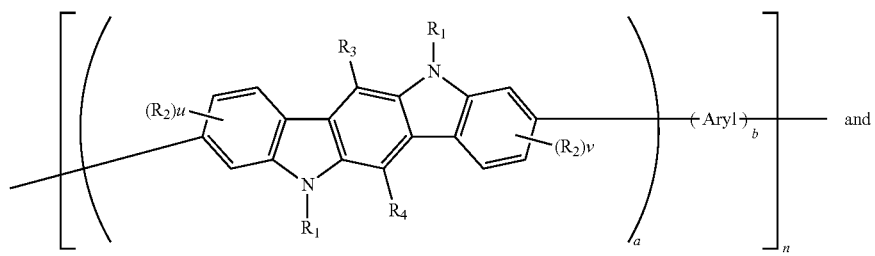

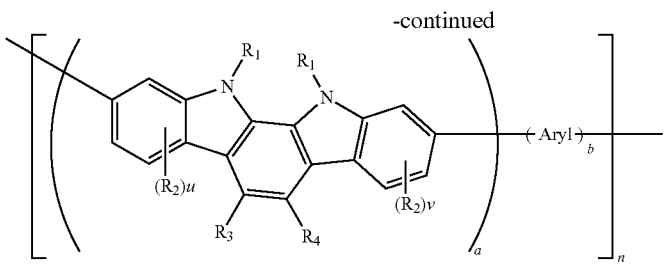

wherein $R_1$-$R_4$ are, independently at each occurrence, alkyl, heteroalkyl aromatic groups, or heteroaromatic groups and u and v are the number of substituents on the benzene ring and are, independently, 1, 2, or 3. In one embodiment, one or more nonadjacent methyl or methylene groups can be replaced by —O—, —S—, —NR'—, or an aromatic or heteroaromatic ring.

Figure 2:
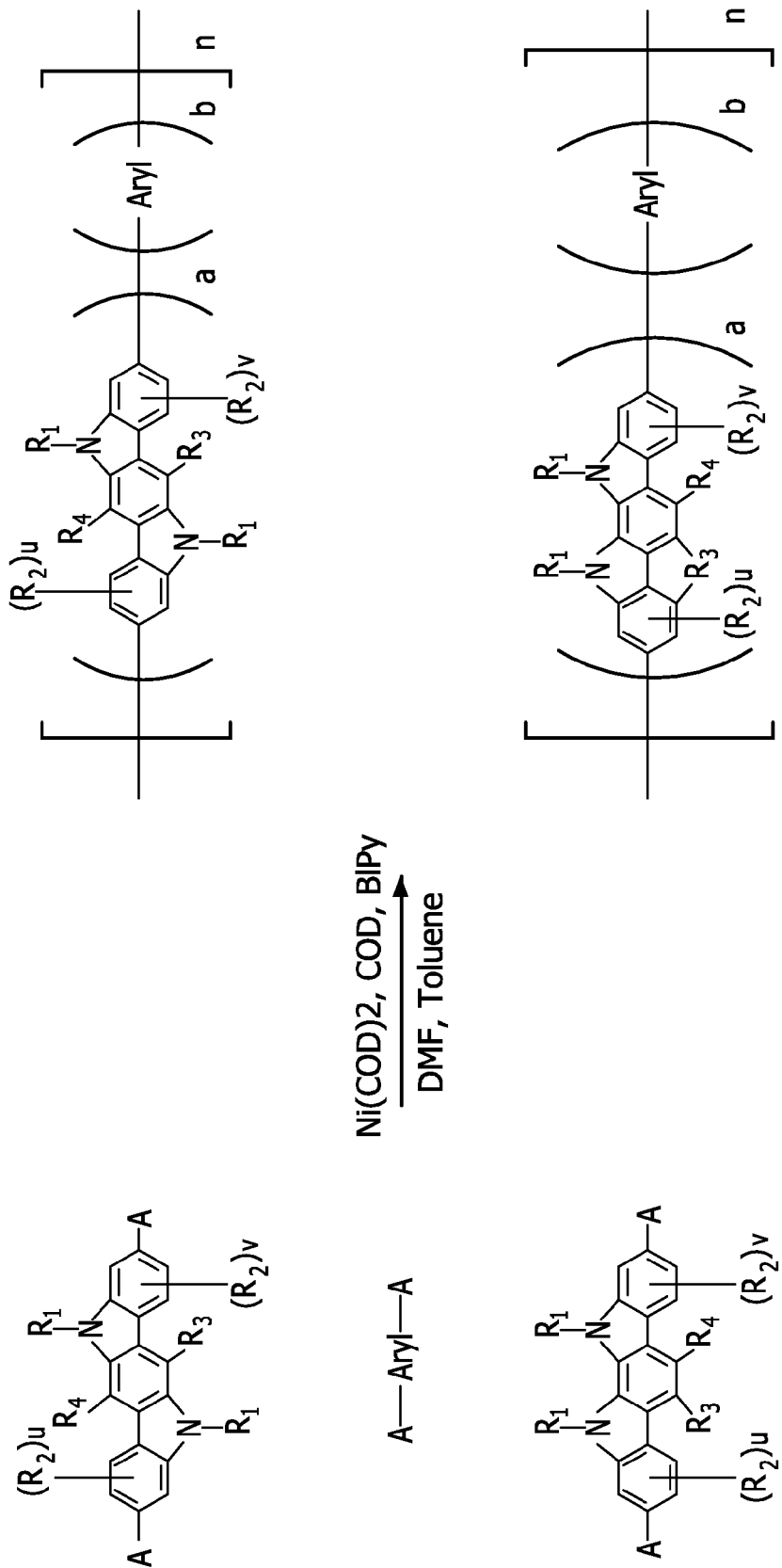
FIG. 2 shows the method known as Yamamoto Polymerization for preparation of indolocarbazole-based polymers, wherein A is the function group and can be selected from bromo, chloro, and iodo group.

FIG. 2 shows the method known as Yamamoto Polymerization for preparation of indolocarbazole-based charge transport polymers, wherein A is the function group and can be selected from bromo, chloro, and iodo group. In one embodiment, a polymer has at least 5 repeating units. Derivatives and conjugates of indolocarbazole polymers may also be desirable for use in charge transport layers, such as hole transport layers.

To make a hole transport polymer, conjugate, or derivative thereof based on indolocarbazole in different applications, solubility control is a consideration. When poly(indolocarbazole) is used in the blend with another charge transport material, solubility of both materials should be compatible to avoid phase separation. Similar-solubility-control-side-chains are chosen for both poly(indolocarbazole) and charge transport material.

For example, when poly{bis[9,9-di(2'-ethylhexyl)fluoren-2-yl]-benzo[1,2-d: 4,5-d]bisoxazole}:

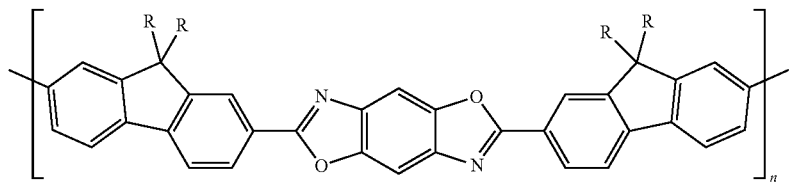

is selected as a charge transport material, for example, an electron transport material, a similar side chain, e.g., from the ethylhexyl group, is selected for poly(indolocarbazole) so that both materials can be easily soluble in the same solvent such as toluene.

When a multiple layer device structure is used, the desired poly(indolocarbazole) should have different solubility as the electron transport material to prevent solvent erosion from solution of electron transport material coated on the top of it. For example, when toluene soluble poly{bis[9,9-di(2'-ethylhexyl)fluoren-2-yl]-benzo[1,2-d: 4,5-d']bisoxazole} is chosen as an electron transport material, the selection of the side chain of poly(indolocarbazole) should make it insoluble in toluene. We use more polar side chain such as 2-[2-(2-methoxyethoxy)ethoxy]ethyl group as a side chain for poly(indolocarbazole) to make it soluble in chlorinated solvent such as tetrachloroethane, while insoluble in toluene.

Compositions comprising dihalogen indolocarbazole monomers, dihalogen indolocarbazole-based polymers, or combinations thereof include a solvent, a processing aid, or combinations thereof. These compositions can be in any form, including, but not limited to solvents, emulsions, and colloidal dispersions.

The compositions can further comprise a charge transporting material, a charge blocking material, or combinations thereof. In some embodiments, the monomers are used to form a hole transport material. Hole transport, hole injection, and electron-withdrawing are used synonymously in this disclosure, and refer to a material that facilitates migration of positive charges through the material with relative efficiency and small loss of charge.

In some embodiments, the polymers are used to form a layer in an organic electronic device.

Organic electronic devices comprising dihalogen indolocarbazole monomers or derivatives thereof; or dihalogen indolocarbazole-based polymers, or conjugates thereof, or derivatives thereof are also provided. In some embodiments, the monomer or the polymer forms a buffer layer, preferably the buffer layer is a hole transport layer. Devices include, but are not limited to light-emitting diodes, light-emitting diode displays, diode lasers, photodetectors, photoconductive cells, photoresistors, photoswitches, phototransistors, phototubes, IR-detectors, photovoltaic devices, solar cells, light sensors, photoconductors, electrophotographic devices, and organic transistors.

In one embodiment, compositions are provided comprising the above-described compounds and at least one solvent, processing aid, charge transporting material, or charge blocking material. These compositions can be in any form, including, but not limited to solvents, emulsions, and colloidal dispersions.

Device

Figure 20:
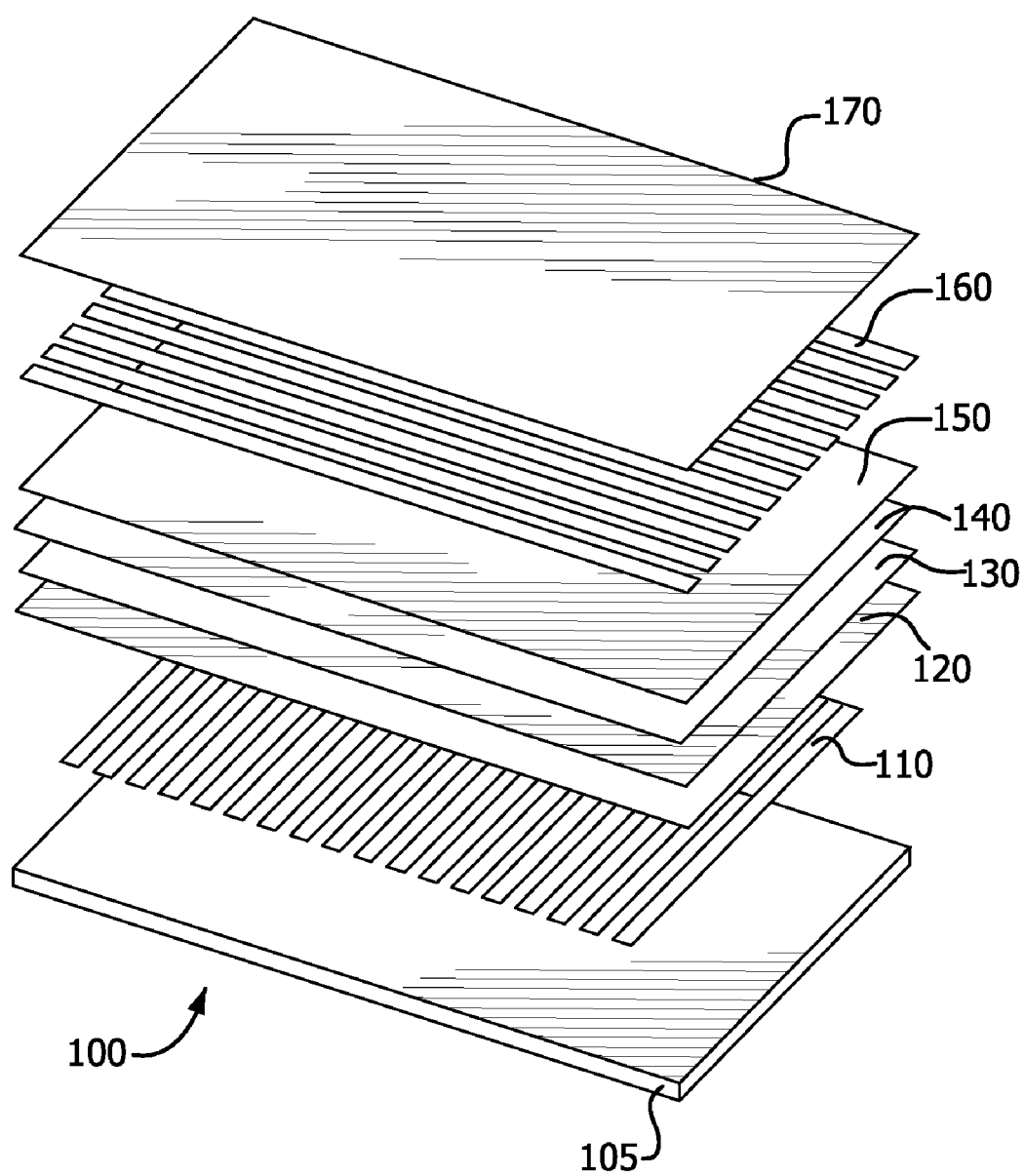
FIG. 20 is a schematic diagram of an organic electronic device.

Referring to FIG. 20, an exemplary organic electronic device 100 is shown. The device 100 includes a substrate 105. The substrate 105 may be rigid or flexible, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. Anode layers may be deposited as lines. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8, 10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in *Flexible Light-Emitting Diodes Made From Soluble Conducting Polymer, Nature* 1992, 357, 477-479. At least one of the anode and cathode should be at least partially transparent to allow the generated light to be observed.

An optional buffer layer 120, such as hole transport materials, may be deposited over the anode layer 110, the latter being sometimes referred to as the "hole-injecting contact layer." Examples of hole transport materials suitable for use as the layer 120 have been summarized, for example, in Kirk Othmer, Encyclopedia of Chemical Technology, Vol. 18, 837-860 ($4^{th}$ ed. 1996). Both hole transporting "small" molecules as well as oligomers and polymers may be used. Hole transporting molecules include, but are not limited to: N,N' diphenyl-N,N'-bis(3-methylphenyl)-[1,1'-biphenyl]-4,4'-diamine (TPD), 1,1 bis[(di-4-tolylamino) phenyl]cyclohexane (TAPC), N,N' bis(4-methylphenyl)-N,N'-bis(4-ethylphenyl)-[1,1'-(3,3'-dimethyl)biphenyl]-4,4'-diamine (ETPD), tetrakis-(3-methylphenyl)-N,N,N',N'-2,5-phenylenediamine (PDA), a-phenyl 4-N,N-diphenylaminostyrene (TPS), p (diethylamino)benzaldehyde diphenylhydrazone (DEH), triphenylamine (TPA), bis[4 (N,N-diethylamino)-2-methylphenyl](4-methylphenyl)methane (MPMP), 1 phenyl-3-[p-(diethylamino) styryl]-5-[p-(diethylamino)phenyl]pyrazoline (PPR or DEASP), 1,2 trans-bis(9H-carbazol-9-yl)cyclobutane (DCZB), N,N,N',N' tetrakis(4-methylphenyl)-(1,1'-biphenyl)-4,4'-diamine (TTB), and porphyrinic compounds, such as copper phthalocyanine. Useful hole transporting polymers include, but are not limited to, polyvinylcarbazole, (phenylmethyl)polysilane, and polyaniline. Conducting polymers are useful as a class. It is also possible to obtain hole transporting polymers by doping hole transporting moieties, such as those mentioned above, into polymers such as polystyrenes and polycarbonates.

An organic layer 130 may be deposited over the buffer layer 120 when present, or over the first electrical contact layer 110. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material (e.g., in layer 130). Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the devices of the invention, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in *Synth. Met.* 2001, 116 (1-3), 379-383, and Campbell et al., in Phys. Rev. B, Vol. 65 085210.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Lithium-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be a layer (not shown) between the anode 110 and hole transport layer 120 to facilitate positive charge transport and/or band-gap matching of the layers, or to function as a protective layer. Other layers that are known in the art or otherwise may be used. In addition, any of the above-described layers may comprise two or more sub-layers or may form a laminar structure. Alternatively, some or all of anode layer 110 the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; hole transport layer 120, 50-2000 Å, in one embodiment 200-1000 Å; photoactive layer 130, 10-2000 Å, in one embodiment 100-1000 Å; layers 140 and 150, 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

Devices can be prepared employing a variety of techniques. These include, by way of non-limiting exemplification, vapor deposition techniques and liquid deposition. Devices may also be sub-assembled into separate articles of manufacture that can then be combined to form the device.

Note that not all of the activities described above in the general description are required, that a portion of a specific activity may not be required, and that one or more further activities may be performed in addition to those described. Still further, the order in which activities are listed are not necessarily the order in which they are performed.

DEFINITIONS

The term "monomer" refers to a compound capable of being polymerized. The term "monomeric unit" refers to units which are repeated in a polymer.

The term "polymer" is intended to mean a material having at least one repeating monomeric unit. The term includes homopolymers having only one kind of monomeric unit, and copolymers having two or more different monomeric units. Copolymers are a subset of polymers.

The term "group" is intended to mean a part of a compound, such as a substituent in an organic compound or a ligand in a metal complex. The prefix "hetero" indicates that one or more carbon atoms have been replaced with a different atom. The term "alkyl" is intended to mean a group derived from an aliphatic hydrocarbon having one point of attachment.

As used herein, the term "alkyl" refers to a monovalent straight or branched chain hydrocarbon group having from one to about 100 carbon atoms, including methyl, ethyl, n-propyl, isopropyl, n-butyl, isobutyl, tert-butyl, n-hexyl, and the like.

As used herein, "heteroaryl" refers to aromatic rings containing one or more heteroatoms (e.g., N, O, S, or the like) as part of the ring structure, and having in the range of 5 up to 14 carbon atoms and "substituted heteroaryl" refers to heteroaryl groups further bearing one or more substituents as set forth above.

Aryl is any type of substituted or unsubstituted aromatic group; a and b are a statistical percentage of indolocarbazole unit and aryl group. The term "aryl" is intended to mean a group derived from an aromatic hydrocarbon having one point of attachment, and aryl can be one or a combination of several different aromatic groups; n is the number of the repeating units and can be from 3-1000.

The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms which are joined by a bond).

The use of "a" or "an" are employed to describe elements and components of the invention. This is done merely for convenience and to give a general sense of the invention. This description should be read to include one or at least one and the singular also includes the plural unless it is obvious that it is meant otherwise.

The term "active" when referring to a layer or material is intended to mean a layer or material that exhibits electronic or electro-radiative properties. An active layer material may emit radiation or exhibit a change in concentration of electron-hole pairs when receiving radiation. Thus, the term "active material" refers to a material which electronically facilitates the operation of the device. Examples of active materials include, but are not limited to, materials which conduct, inject, transport, or block a charge, where the charge can be either an electron or a hole. Examples of inactive materials include, but are not limited to, planarization materials, insulating materials, and environmental barrier materials.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

The term "layer" is used interchangeably with the term "film" and refers to a coating covering a desired area. The area can be as large as an entire device or a specific functional area such as the actual visual display, or as small as a single sub-pixel. Films can be formed by any conventional deposition technique, including vapor deposition and liquid deposition. Liquid deposition techniques include, but are not limited to, continuous deposition techniques such as spin coating, gravure coating, curtain coating, dip coating, slot-die coating, spray-coating, and continuous nozzle coating; and discontinuous deposition techniques such as ink jet printing, gravure printing, and screen printing.

The term "organic electronic device" is intended to mean a device including one or more semiconductor layers or materials. Organic electronic devices include, but are not limited to: (1) devices that convert electrical energy into radiation (e.g., a light-emitting diode, light emitting diode display, diode laser, or lighting panel), (2) devices that detect signals through electronic processes (e.g., photodetectors photoconductive cells, photoresistors, photoswitches, phototransistors, phototubes, infrared ("IR") detectors, or biosensors), (3) devices that convert radiation into electrical energy (e.g., a photovoltaic device or solar cell), and (4) devices that include one or more electronic components that include one or more organic semiconductor layers (e.g., a transistor or diode). The term device also includes coating materials for memory storage devices, antistatic films, biosensors, electrochromic devices, solid electrolyte capacitors, energy storage devices such as a rechargeable battery, and electromagnetic shielding applications.

The term "substrate" is intended to mean a workpiece that can be either rigid or flexible and may include one or more layers of one or more materials, which can include, but are not limited to, glass, polymer, metal, or ceramic materials, or combinations thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will Control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

EXAMPLES

The concepts described herein will be further described in the following examples, which do not limit the scope of the invention described in the claims.

Example 1

Preparation of 1,4-Bis(2'-nitro-4'-chlorophenyl)benzene

Figure 3:
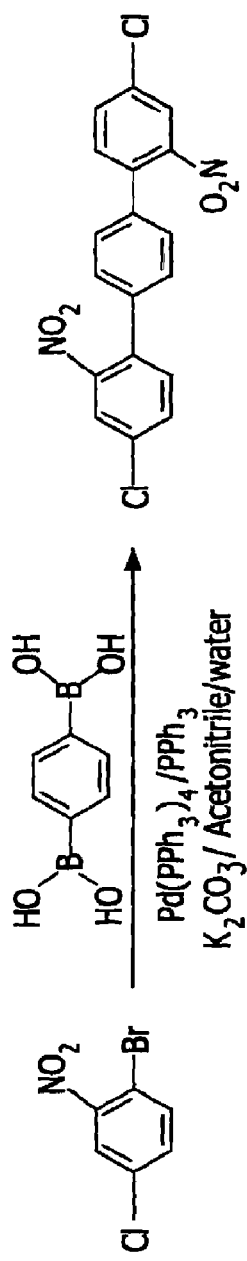
FIG. 3 shows the reaction scheme for synthesis of 1,4-Bis (2'-nitro-4'-chlorophenyl)benzene.

FIG. 3 shows the reaction scheme for synthesis of 1,4-Bis (2'-nitro-4'-chlorophenyl)benzene.

A one liter flask charged with 1-bromo-4-chloro-2-nitrobenzene (91.76 g, 388.0 mmol), 1,4-phenylenebisboronic acid (32.16 g, 194.0 mmol), potassium carbonate (55.28 g, 400.0 mmol), benzyltriethylammonium chloride (1000 mg, 4.4 mmol), $PPh_3$ (1.20 g, 4.56 mmol), and $Pd(PPh_3)_4$ (1.20 g, 1.08 mmol) was flushed with nitrogen. Acetonitrile (300 mL) and water (150 mL) was then added.

After stirring at room temperature (RT) under nitrogen for 5 minutes, the mixture was heated to and maintained at reflux (oil bath temp 90° C.) for 68 hours. The mixture was allowed to cool to room temperature and poured into 10% HCl solution (400 mL) then filtered off the precipitate. The precipitate was washed with water (150 mL) and allowed to air dry. The dry powder was rinsed with cool THF and dried again to afford 39.25 g (52%) of the desired product.

$^1$H NMR (500 MHz, DMF-$d_7$) δ ppm: 8.24 (d, J=2.0 Hz, 2H), 7.94 (dd, J=8.3, 2.0 Hz, 2H), 7.57 (s, 4H), 7.73 (d, J=8.3 Hz, 2H).

Example 2

Preparation of 3,9-Dichloro-5,11-dihydromdolo[3,2-b]carbazole

Figure 4:
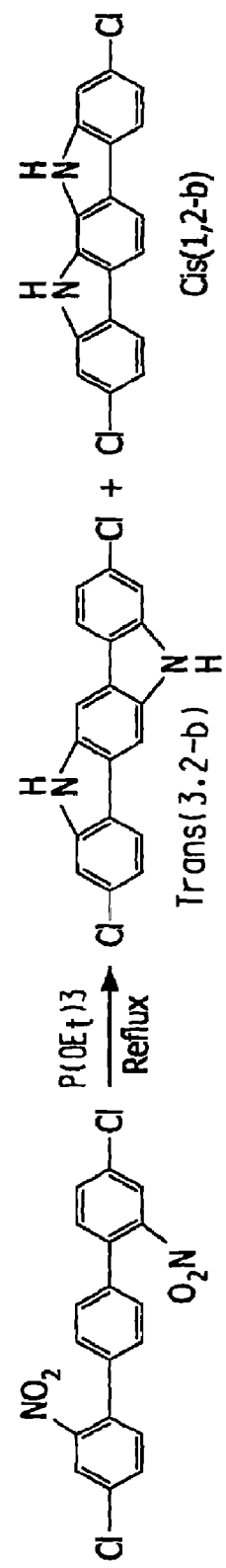
FIG. 4 shows the reaction scheme for synthesis of 3,9-Dichloro-5,11-dihydromdolo[3,2-b]carbazole

FIG. 4 shows the reaction scheme for synthesis of 3,9-Dichloro-5,11-dihydromdolo[3,2-b]carbazole.

A 500-mL flask charged with 1,4-bis(2'-nitro-4'-chlorophenyl)benzene (36.97 g, 95.0 mmol) was flushed with argon. Triethylphosphite (150 mL) was then added. After stirring at room temperature (RT) under argon for 5 minutes, the mixture was heated to and maintained at oil bath temp 153° C. for 21 hours. The mixture was allowed to cool to room temperature and poured into a mixture of ethanol (500 mL) and water (50 mL). The precipitate was collected, washed with ethanol (50 mL) and dried to give the cis[I,2-b]product (4.66 g, 15%) as a pale yellowish powder. Then water (300 mL) was added to the filtrate. The precipitate was collected, and washed with cool ethanol (50 mL) and dried to give the trans[3,2-b]product (25.49 g, 82.5%) as a brownish powder.

Trans[3,2-b] Isomer:
$^1$H NMR (500 MHz, THF-$d_8$) δ 7.19 (dd, J=8.3, 1.5 Hz, 2H), 7.55 (d, J=1.34 Hz, 2H), 7.88 (s, 2H), 8.06 (d, J=8.3 Hz, 2H), 10.28 (s, 2H).

Cis[I,2-b] Isomer:
$^1$H NMR (500 MHz, THF-$d_8$) δ 7.10 (dd, J=8.3, 1.44 Hz, 2H), 7.40 (d, J=1.44 Hz, 2H), 8.02 (s, 2H), 8.06 (d, J=8.3 Hz, 2H), 10.30 (s, 2H).

Example 3

Preparation of N,N'-Di(2'-ethylhexyl)-3,9-dichloro-5,11-dihydroindolo[3,2-b]carbazole FIG. 5 shows the reaction scheme for synthesis of N,N'-Di (2'-ethylhexyl)-3,9-dichloro-5,11-dihydroindolo[3,2-b]carbazole.

A 250-mL flask charged with 3,9-dichloro-5,11-dihydroindolo[3,2-b]carbazole (9.76 g, 30.0 mmol) and potassium hydroxide (16.84 g, 300.0 mmol) was flushed with nitrogen. THF (100 mL) was then added. The mixture was heated to and maintained at 80° C. (oil bath temp) for 2 hours. 2-Ethylhexylbromide (23.17 g, 120.0 mmol) was added to the reaction mixture and maintained at the same conditions (80° C.) for 20 hours. The mixture was allowed to cool to room temperature and poured into water (150 mL), and then extracted with hexanes (3×150 mL). The combined organic layer was washed with water (2×150 mL), brine (150 mL), and then dried over magnesium sulfate. The crude product was purified by column chromatography using hexanes as eluent on silica gel to afford the desired product.

$^1$H NMR (500 MHz, GDC13) δ ppm: 8.00 (d, J=8.25 Hz, 2H), 7.87 (s, 2H), 7.49 (d, J=1.70 Hz, 2H), 7.44 (dd, J=8.25, 1.70 Hz, 2H), 4.49 (d, J=7.63 Hz, 4H), 1.89 (m, 2H), 0.61-1.05 (m, 16H), 0.50-0.61 (m, 12H), $^{13}$C NMR (125 MHz, CDC13) δ ppm: 143.54, 130.83, 130.52, 124.50, 123.78, 120.95, 120.67, 113.41, 112.10, 52.13, 38.27, 29.73, 27.68, 23.38, 22.84, 13.87, 10.29.

Example 4

Preparation of N,N'-Di(2'-ethylhexyl)-3,8-dichloro-5,6-dihydromdolo[1,2-b]carbazole FIG. 6 shows the reaction scheme for synthesis of N,N'-Di(2'-ethylhexyl)-3,8-dichloro-5,6-dihydromdolo[1,2-b]carbazole.

A 50-mL flask charged with 3,8-dichloro-5,6-dihydroindolo[1,2-b]carbazole (1.95 g, 6.0 mmol) and potassium hydroxide (4.04 g, 72 mmol) was flushed with nitrogen. THF (20 mL) was then added. The mixture was heated to and maintained at 80° C. (oil bath temperature) for 2 hours. 2-Ethylhexylbromide (6.95 g, 26 mmol) was added to the reaction mixture and maintained at the same conditions (80° C.) for 17 hours.

The mixture was allowed to cool to room temperature and poured into water (50 mL), and then extracted with hexanes (3×50 mL). The combined organic layer was washed with water (2×50 mL), brine (50 mL), and then dried over magnesium sulfate.

The crude product was purified by column chromatography using hexanes as an eluent on silica gel to afford the desired product.

$^1$H NMR (500 MHz, CDC13) δ ppm: 8.04 (d, J=8.20 Hz, 2H), 7.84 (s, 2H), 7.33 (d, J=1.38 Hz, 2H), 7.17 (dd, J=8.20, 1.38 Hz, 2H), 4.13 (m, 4H), 2.12 (m, 2H), 1.10-1.50 (m, 16H), 0.75-1.00 (m, 12H).

Example 5

Figure 7:
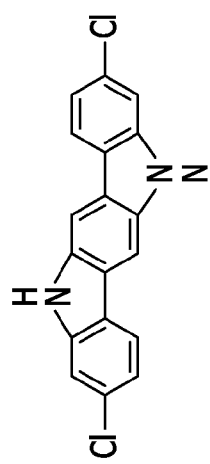
FIG. 7 shows the reaction scheme for synthesis of N,N'-bis [2-[2-(2-methoxyethoxy)ethoxy]ethyl]-3,9-dichloro-5,11-dihydroindolo[3,2-b]carbazole.
Figure 7:
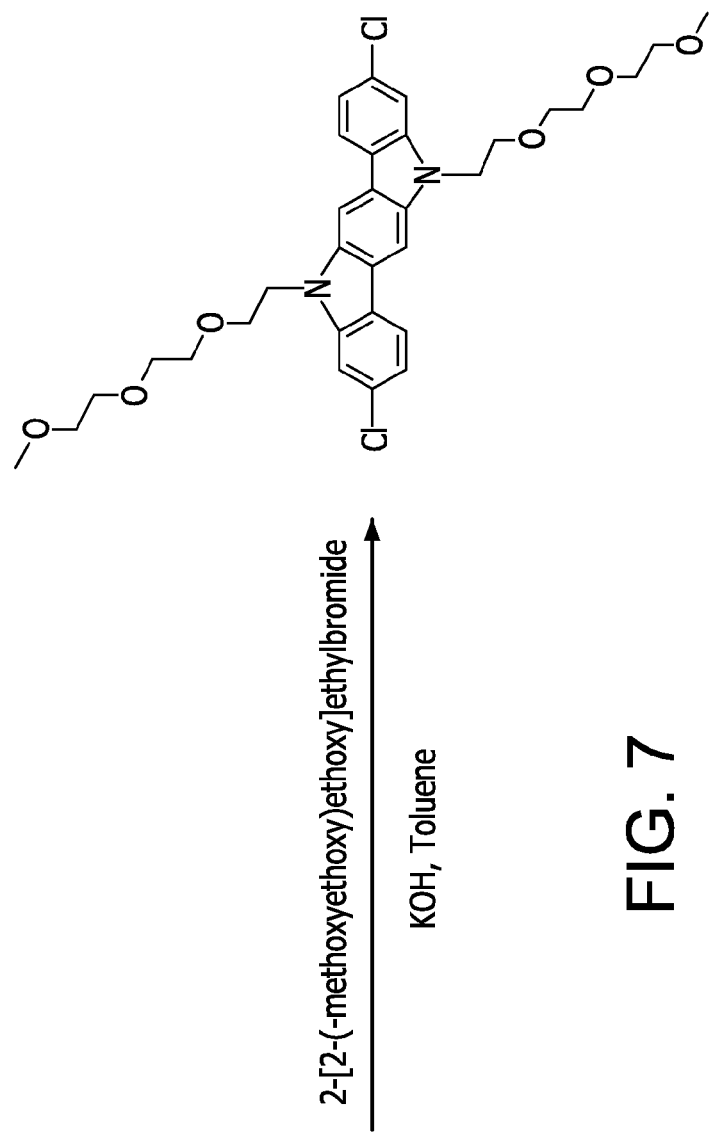

Preparation of N,N'-bis[2-[2-(2-methoxyethoxy)ethoxy]ethyl]-3,9-dichloro-5,11-dihydroindolo[3,2-b]carbazole FIG. 7 shows the reaction scheme for synthesis of N,N'-bis[2-[2-(2-methoxyethoxy)ethoxy]ethyl]-3,9-dichloro-5,11-dihydroindolo[3,2-b]carbazole.

Example 6

General Procedure of Polymerization Through the Yamamoto Reaction

FIG. 2 shows the method known as Yamamoto Polymerization for indolocarbazole-based charge transport material, wherein A is the function group and can be selected from bromo, chloro, and iodo group.

A Schlenck flask equipped with a stirring bar was charged with bis(I,5-cyclooctadiene)-nickel(O) (2.02 equiv.), 2,2'-bipyridyl (2.02 equiv.), 1,5-cyclooctadiene (2.02 equiv.) and DMF (¼ of toluene volume). The mixture was stirred under an argon atmosphere at 65° C. for 30 minutes and then the temperature was increased to 70° C. A solution of the monomer(s) (1.00 equiv.) in toluene ([monomer]=I/6 M) was added to the mixture, which was then allowed to stir for 16 to 115 hours. Bromobenzene was added and the reaction mixture was allowed to stir for 1 hour. After the mixture was allowed to cool to room temperature, concentrated hydrochloric acid was added and the reaction mixture was allowed to stir for a further 5 minutes. The whole mixture was poured slowly into methanol to precipitate the polymer. The polymer/methanol mixture was then filtered. The polymer isolated by filtration was then further re-precipitated into methanol from chloroform solution. The polymer was now taken up again in chloroform for washing with KOH (10 wt % aqueous), EDTA (aqueous, pH 7.0), and de-ionized water. The organic layer was passed through a 5 μm filter and precipitated into methanol. The collected solid was dried under reduced pressure at 45° C. overnight.

Example 6a

Poly(N,N'-Di(2'-ethylhexyl)-5,11-dihydroindolo[3,2-b]carbazole)

Figure 8:
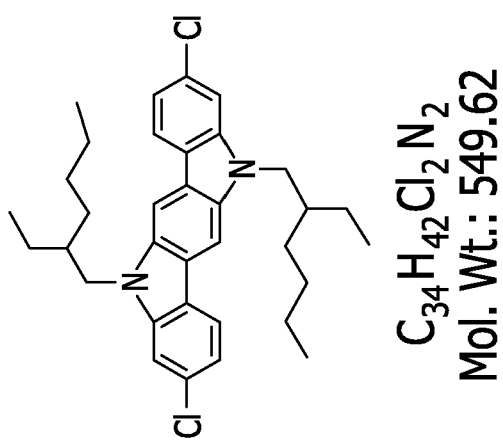
FIG. 8 shows the reaction scheme for synthesis of poly(N, N'-Di(2'-ethylhexyl)-5,11-dihydroindolo[3,2-b]carbazole).
Figure 8:
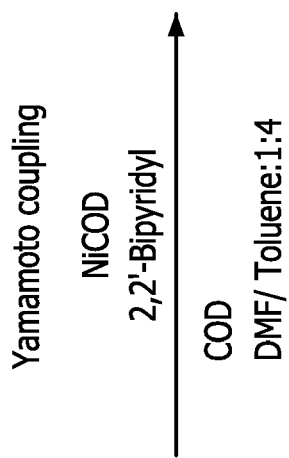
Figure 8:
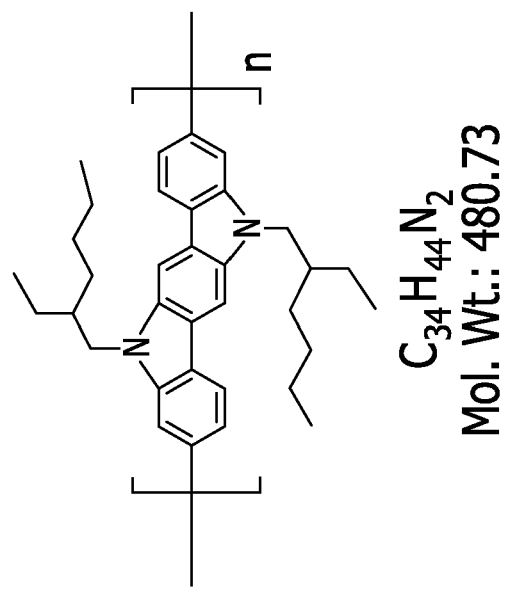

FIG. 8 shows the reaction scheme for synthesis of poly(N,N'-Di(2'-ethylhexyl)-5,11-dihydroindolo[3,2-b]carbazole). The resulting material was a light yellow solid, having a yield of 75%.

Example 6b

Poly{N,N'-bis[2-[2-(2-methoxyethoxy)ethoxy]ethyl]-5,11-dihydroindolo[3,2-b]carbazole}

Figure 9:
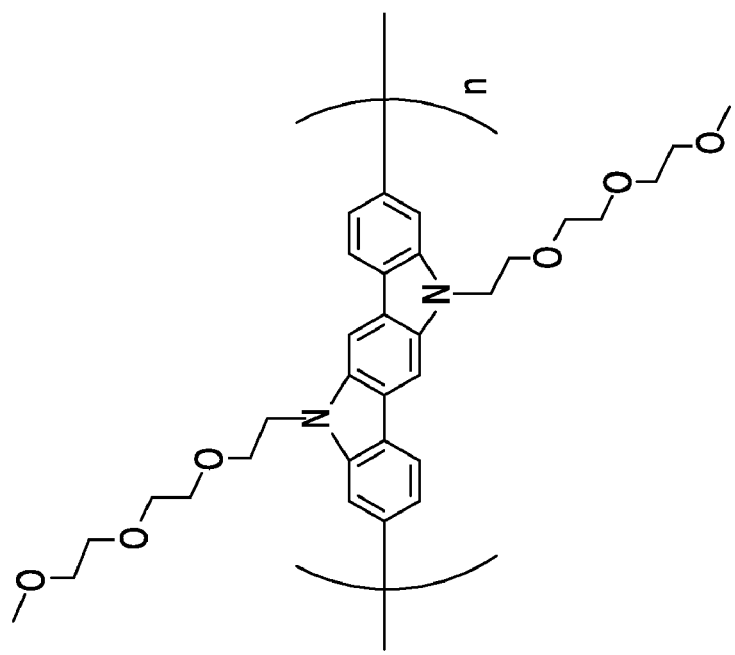
FIG. 9 shows the reaction scheme for synthesis of poly{N, N'-bis[2-[2-(2-methoxyethoxy)ethoxy]ethyl]-5,11-dihydroindolo[3,2-b]carbazole}.
Figure 9:
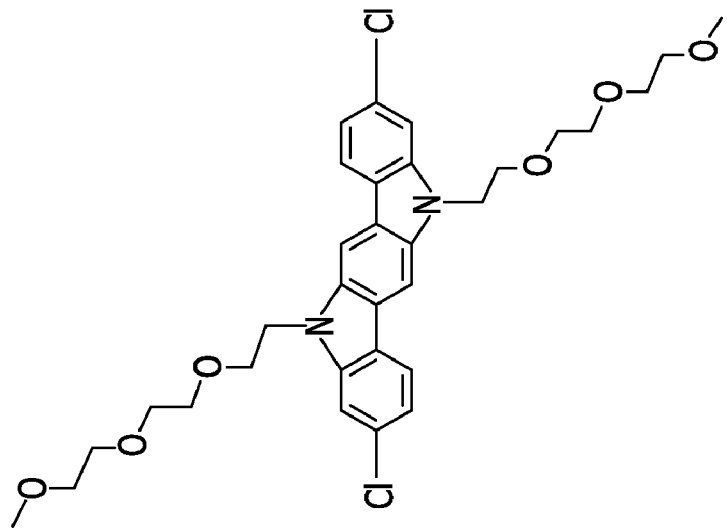

FIG. 9 shows the reaction scheme for synthesis of poly{N,N'-bis[2-[2-(2-methoxyethoxy)ethoxy]ethyl]-5,11-dihydroindolo[3,2-b]carbazole}. The resulting material was a light yellow solid, having a yield of 49%.

Example 6c

Poly{N,N'-bis[2-[2-(2-methoxyethoxy)ethoxy]ethyl]-5,11-dihydroindolo[3,2-b]carbazole-co-[2-[2-(2-methoxyethoxy)ethoxy]ethoxy]-phenylene} (50/50 mole %)

Figure 10:
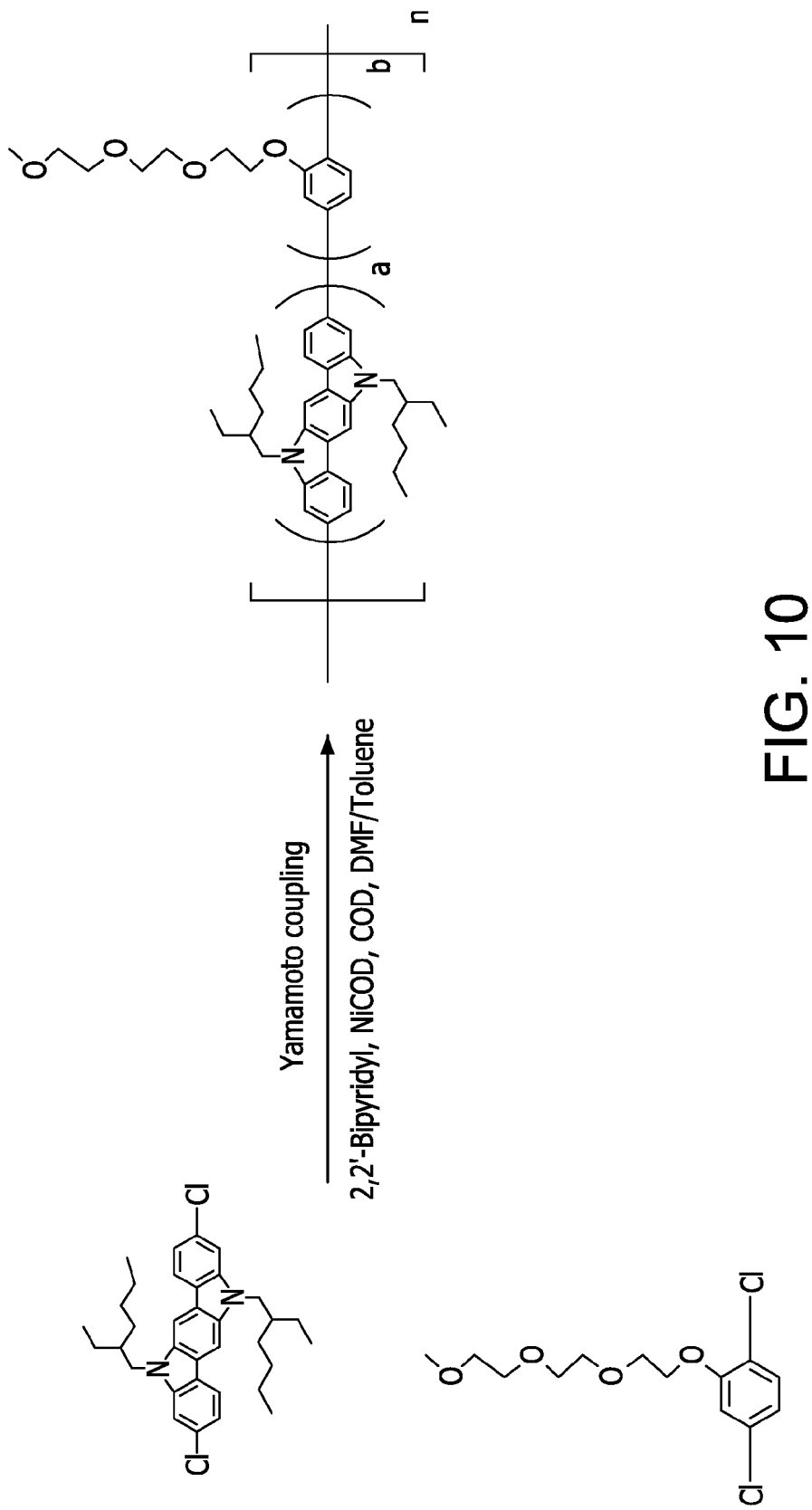
FIG. 10 shows the reaction scheme for synthesis of poly{N,N'-bis[2-[2-(2-methoxyethoxy)ethoxy]ethyl]-5,11-dihydroindolo[3,2-b]carbazole-co-[2-[2-(2-methoxyethoxy) ethoxy]ethoxy]-phenylene}.

FIG. 10 shows the reaction scheme for synthesis of poly{N,N'-bis[2-[2-(2-methoxyethoxy)ethoxy]ethyl]-5,11-dihydroindolo[3,2-b]carbazole-co-[2-[2-(2-methoxyethoxy)ethoxy]ethoxy]-phenylene}. The resulting material was a light yellow solid, having a yield of 62%.

Example 6d

Poly{N,N'-bis[2-[2-(2-methoxyethoxy)ethoxy]ethyl]-5,11-dihydroindolo[3,2-b]carbazole-co-9,9-bis[2-[2-(2-methoxyethoxy)ethoxy]ethyl]-fluorene} (50/50 mole %)

Figure 11:
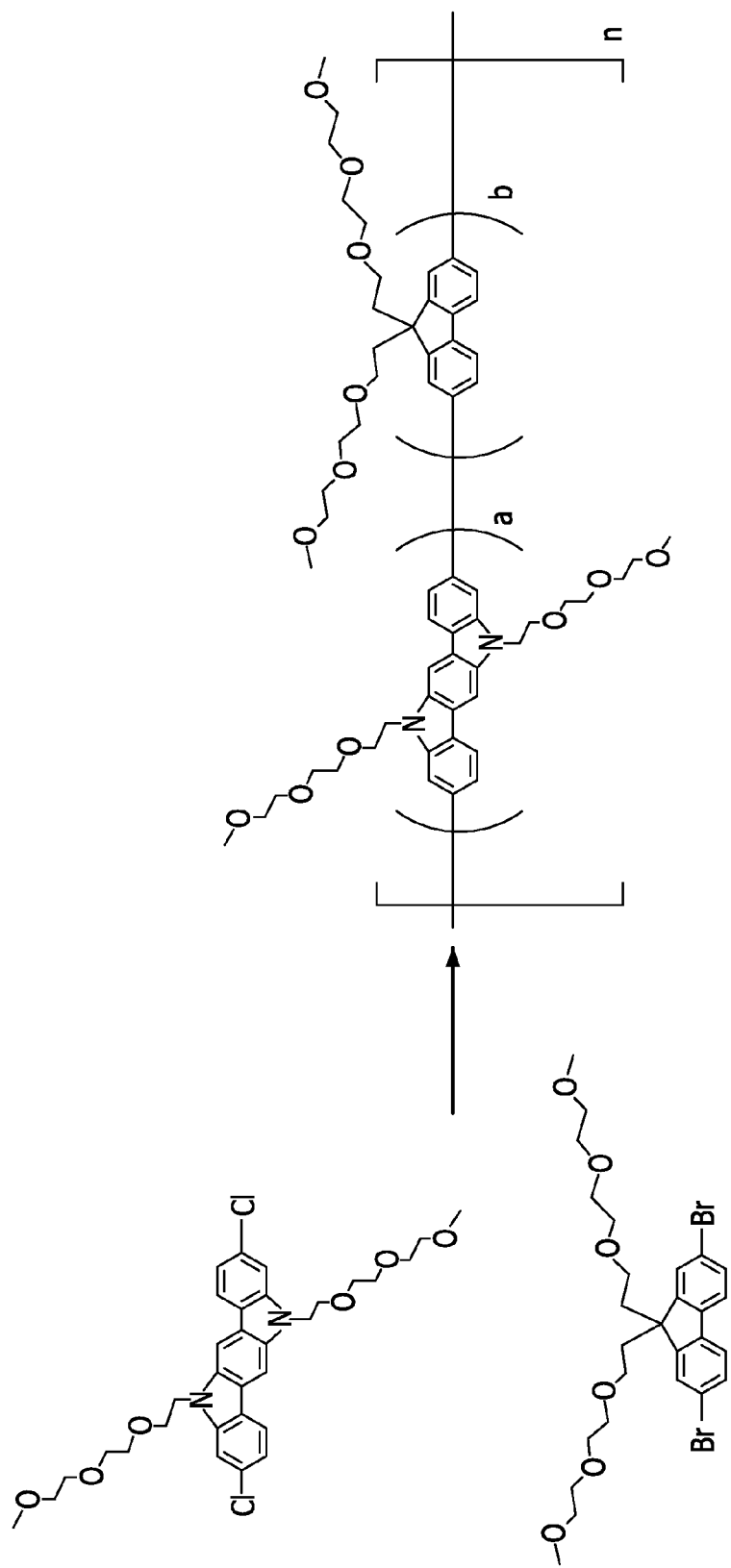
FIG. 11 shows the reaction scheme for synthesis of poly{N,N'-bis[2-[2-(2-methoxyethoxy)ethoxy]ethyl]-5,11-dihydroindolo[3,2-b]carbazole-co-9,9-bis[2-[2-(2-methoxyethoxy)ethoxy]ethyl]-fluorene}.

FIG. 11 shows the reaction scheme for synthesis of poly{N,N'-bis[2-[2-(2-methoxyethoxy)ethoxy]ethyl]-5,11-dihydroindolo[3,2-b]carbazole-co-9,9-bis[2-[2-(2-methoxyethoxy)ethoxy]ethyl]-fluorene}. The resulting material was a light yellow solid, having a yield of 84%.

Example 6e

Poly{9,9-bis[2-[2-(2-methoxyethoxy)ethoxy]ethyl]fluorene}

Figure 12:
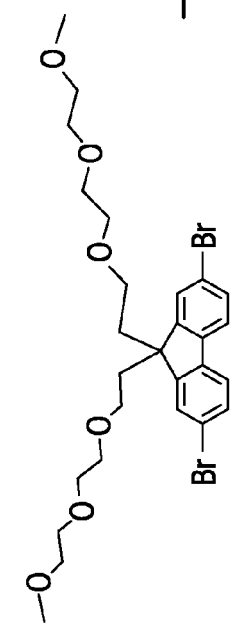
FIG. 12 shows the reaction scheme for synthesis of poly{9, 9-bis[2-[2-(2-methoxyethoxy)ethoxy]ethyl]fluorene}.
Figure 12:
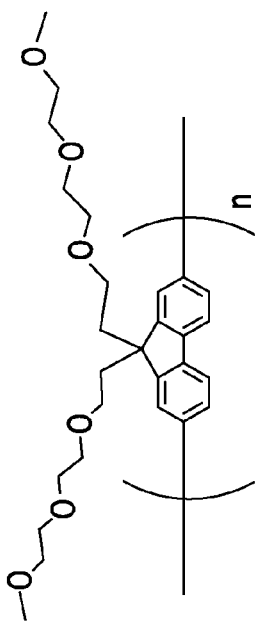

FIG. 12 shows the reaction scheme for synthesis of poly{9,9-bis[2-[2-(2-methoxyethoxy)ethoxy]ethyl]fluorene}. The resulting material was a light yellow solid, having a yield of 88%.

Example 6f

Poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole}

Figure 13:
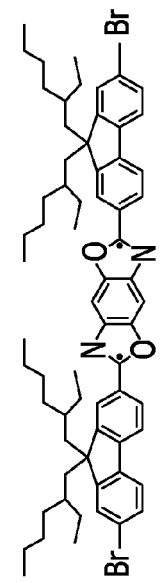
FIG. 13 shows the reaction scheme for synthesis of poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d]bisoxazole}.
Figure 13:
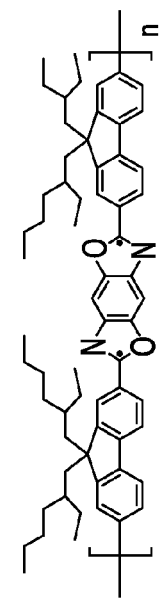

Electron transport material prepared in accordance with FIG. 13. The resulting material was a light yellow solid, having a yield of 87%.

Example 7

Electrochemistry of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole}

Figure 14:
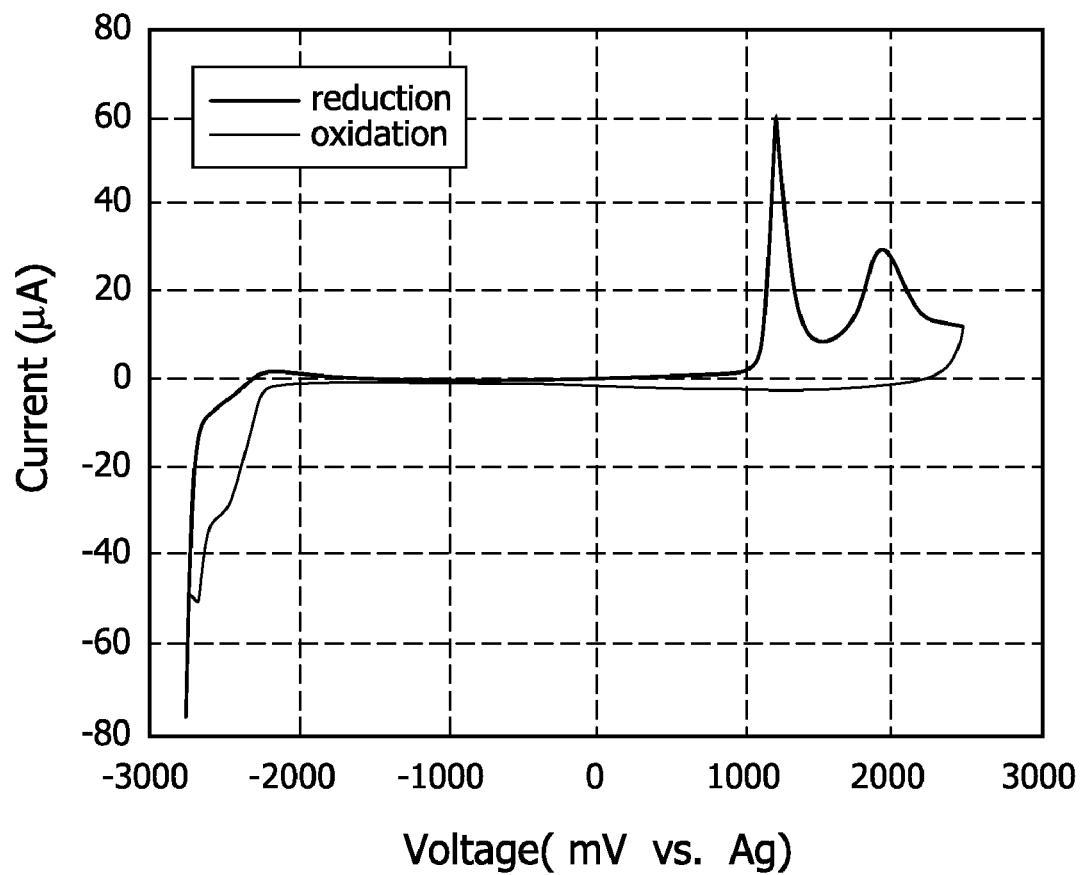
FIG. 14 shows electrochemistry of poly(N,N-diethylhexylindolocarbazole).
Figure 15:
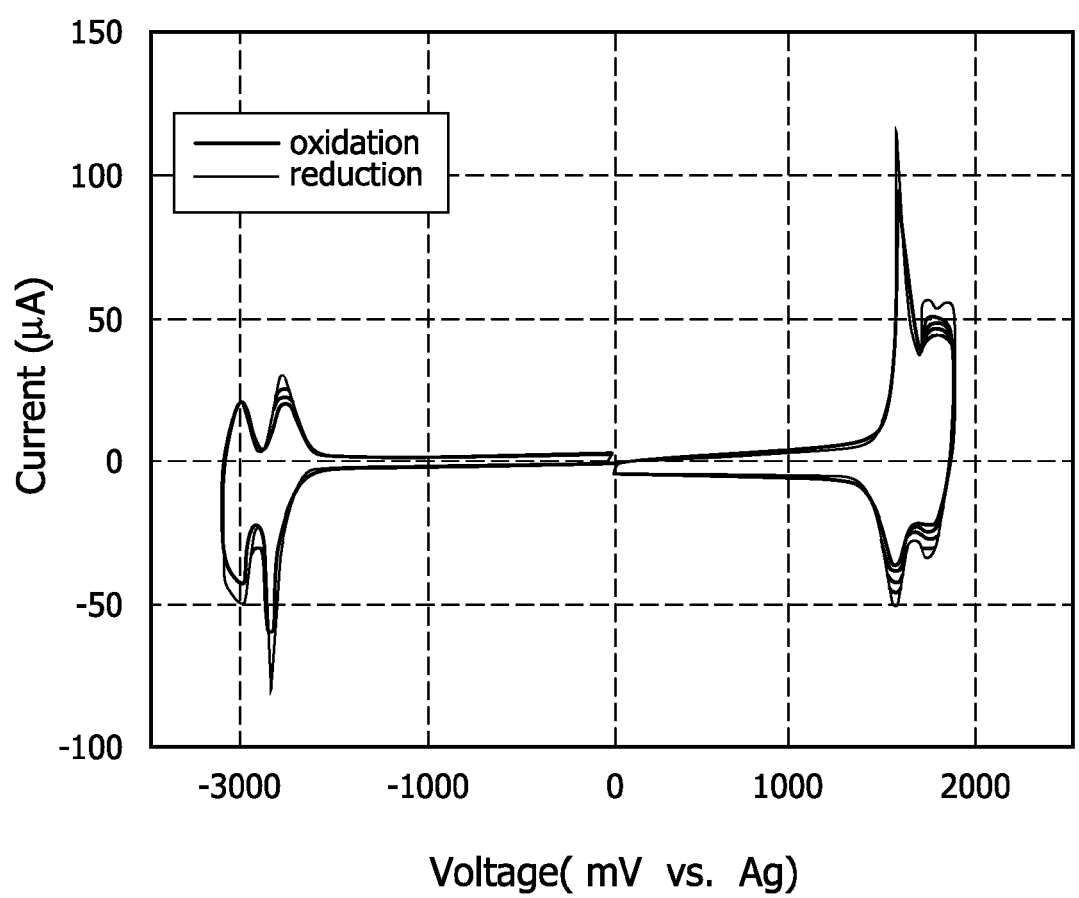
FIG. 15 shows the electrochemistry of poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1, 2-d;4,5-d]bisoxazole}.

FIG. 14 shows that electrochemistry of poly(N,N-diethylhexylindolocarbazole). The energy levels of HOMO and LUMO were estimated to be 5.4 and 2.2 eV, respectively. FIG. 15 shows the electrochemistry of poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole}. The energy levels of HOMO and LUMO were estimated to be 5.8 and 2.8 eV, respectively.

This example demonstrates that a blend of the poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole} can be used for as a charge transport material, e.g., a hole transport material. The HOMO energy level of poly(N,N-diethylhexylindolocarbazole) determined by electrochemistry showed that it is easier to be oxidized, i.e. easier hole injection.

This example also demonstrates that poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole} can be used as an electron transport material. The LUMO energy level of poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole} determined by electrochemistry showed it is easier to be reduced, i.e. easier electron injection.

Example 8

Figure 16:
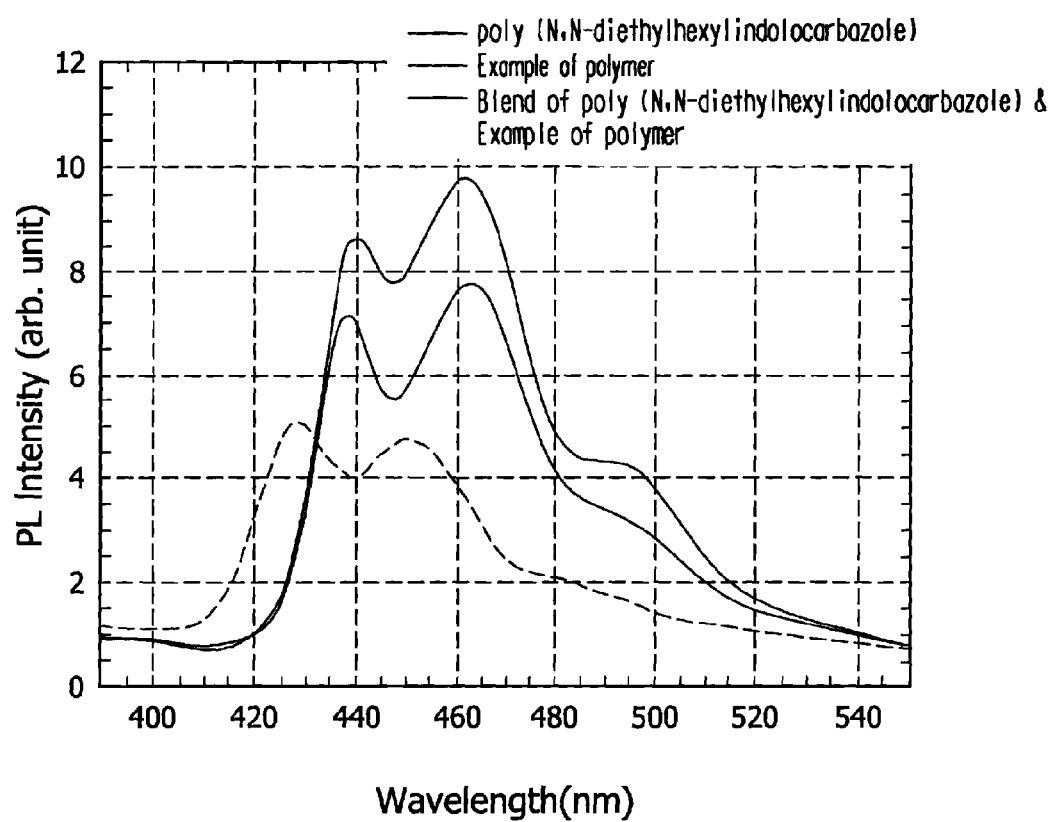
FIG. 16 shows the photoluminescence (PL) spectra of poly (N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1, 2-d;4,5-d']bisoxazole}, individually and blended.

PL spectra of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole}, and PL spectrum of blend for blue LED FIG. 16 shows the PL spectra of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole}, and the PL spectrum of blend for a blue LED. This example demonstrates that poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole} can be blended without causing any photoluminescence quench. The photoluminescence of the blend is mainly from the emission of poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole}.

Example 9

Figure 17:
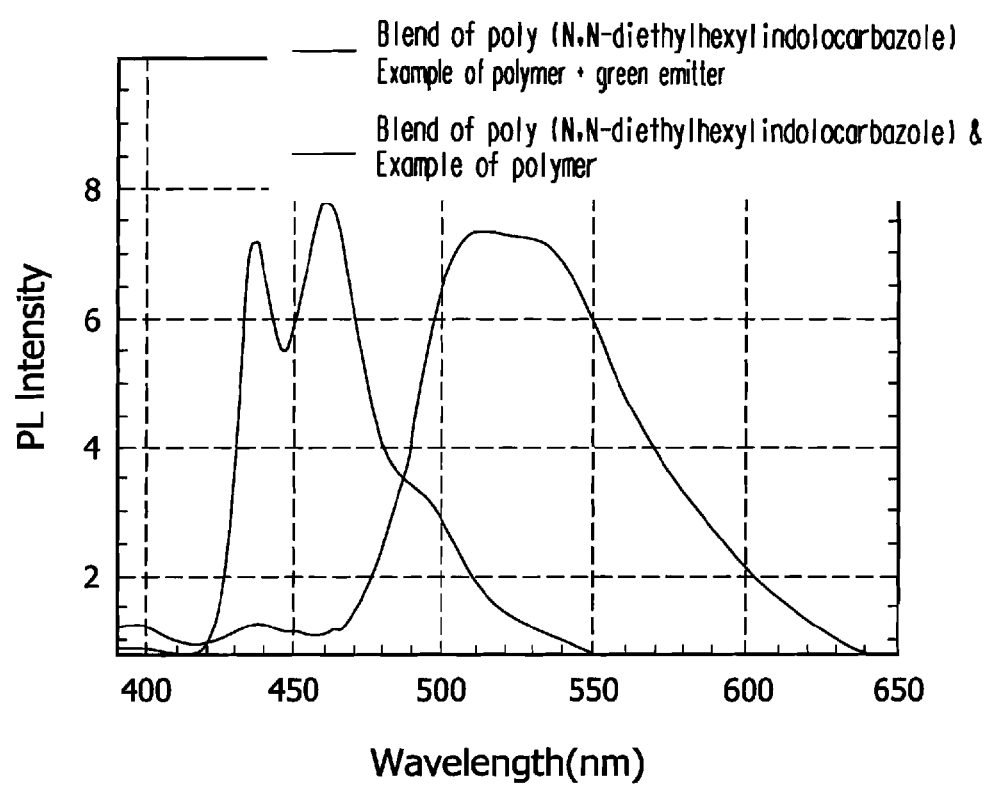
FIG. 17 shows the photoluminescence (PL) spectra of a blend of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole}, and the blend that has been doped with a green emitter.

PL spectra of blend of poly(N,N-diethylhexylindolocarbazole), poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d]bisoxazole} & perylene dicarboxylic acid diisobutyl ester for green LED FIG. 17 shows the PL spectra of blend of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole} & the blend containing perylene dicarboxylic acid diisobutyl ester for green LED. This example demonstrates that a green emissive layer can be formulated by poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-']bisoxazole} blend doped with a low concentration of green emitter.

Example 10

Figure 18:
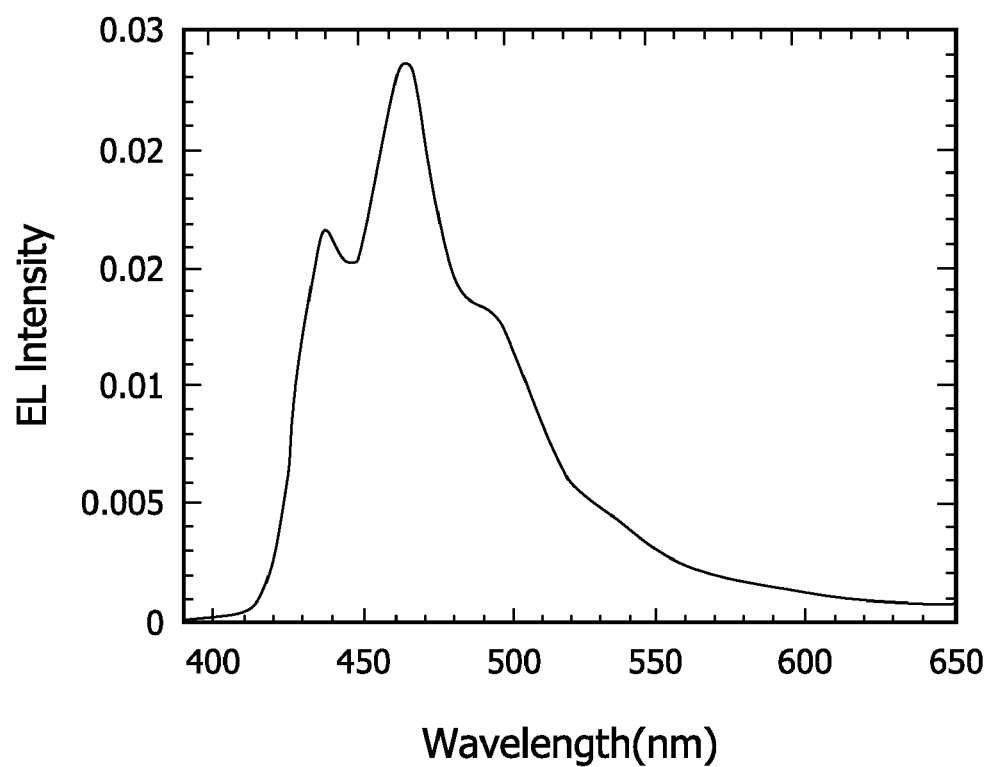
FIG. 18 shows the EL spectra of a blend of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4, 5-d']bisoxazole} for blue LED.

EL device fabrication of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole} blend for blue LED FIG. 18 shows the EL spectrum for a poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d] bisoxazole} blend. This example demonstrates a blue LED can be fabricated by this blend. The low operating voltage of the device confirmed the balance carrier injection.

ITO/PEDT/Blend of HT (poly(N,N-diethylhexylindolocarbazole)) and ET (poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole})/LiF/Al C.I.E. Coordinate: u'=0.143, v'=0.328 Device performance: 200 cd/m2 3.7V0.6 cd/A Example 11

Figure 19:
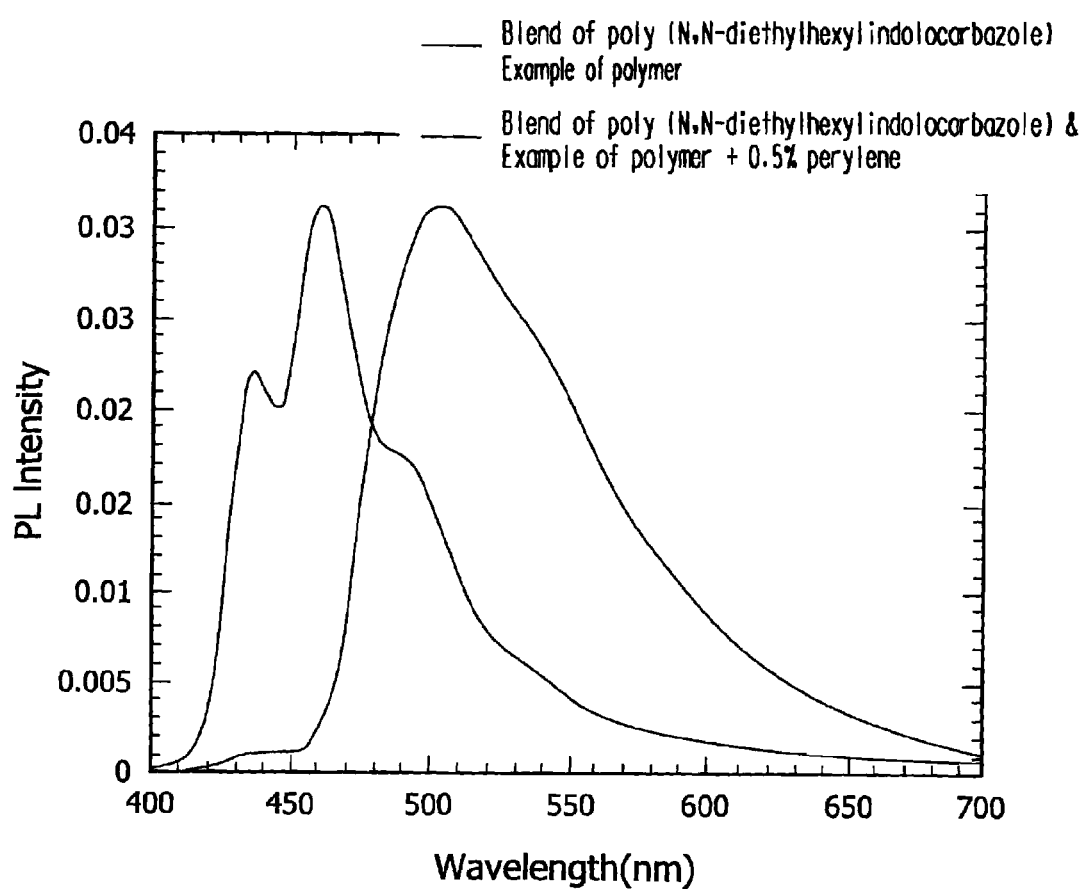
FIG. 19 shows the EL spectra of a blend of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4, 5-d']bisoxazole}, and the blend that has been doped with 0.5% by weight perylene dicarboxylic acid diisobutyl ester for green LED.

EL device fabrication of poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d']bisoxazole} blend and perylene dicarboxylic acid diisobutyl ester dopant for green FIG. 19 shows the EL spectrum for a poly(N,N-diethylhexylindolocarbazole) and poly{2-[9,9-Bis-(2-ethyl-hexyl)-7-methyl-9H-fluoren-2-yl]-6-[9-(2-ethyl-butyl)-9-(2-ethyl-heptyl)-7-methyl-9H-fluoren-2-yl]-benzo[1,2-d;4,5-d'] bisoxazole} blend, and the blend doped with 0.5% by weight perylene dicarboxylic acid diisobutyl ester dopant.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

The invention claimed is:
1. A monomer having Formula I or II:
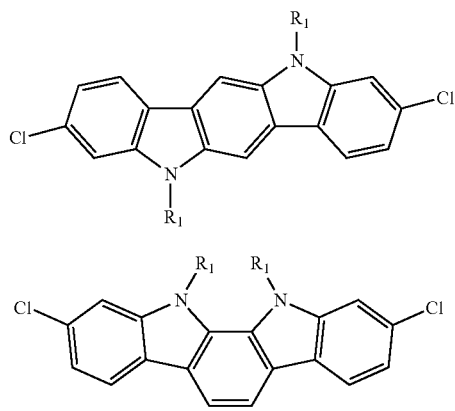
wherein:
R$_1$ is 2' ethylhexyl, or 2-[2-(2-methoxyethoxy)ethoxy]ethyl.
2. The monomer of claim 1, wherein R$_1$ is 2'ethylhexyl.
3. The monomer of claim 1 wherein R$_1$ is 2-[2-(2-methoxyethoxy)ethoxy]ethyl.
4. A material comprising a monomer of claim 1.
5. A compound of the formula
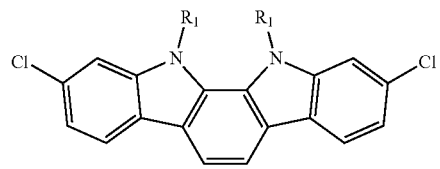
where R1 is H.
* * * * *